US012805797B2

(12) United States Patent
Piraino

(10) Patent No.: US 12,805,797 B2
(45) Date of Patent: Nov. 24, 2026

(54) METHODS AND SYSTEMS FOR MONITORING AND DELIVERING THERAPY TO A PATIENT INCLUDING A DETACHABLE MANIFOLD FOR A MONITOR MODULE

(71) Applicant: Physio-Control, Inc., Redmond, WA (US)

(72) Inventor: Daniel W. Piraino, Seattle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 1055 days.

(21) Appl. No.: 17/961,720

(22) Filed: Oct. 7, 2022

(65) Prior Publication Data

US 2023/0033386 A1 Feb. 2, 2023

Related U.S. Application Data

(63) Continuation of application No. 17/065,765, filed on Oct. 8, 2020, now Pat. No. 11,490,855.

(Continued)

(51) Int. Cl.

*A61B 5/00* (2006.01)
*A61B 5/0205* (2006.01)

(Continued)

(52) U.S. Cl.

CPC .......... *A61B 5/4836* (2013.01); *A61B 5/0006* (2013.01); *A61B 5/0008* (2013.01); *A61B 5/02055* (2013.01); *A61B 5/14551* (2013.01); *A61B 5/303* (2021.01); *A61B 5/308* (2021.01); *A61B 5/339* (2021.01); *A61B 5/6891* (2013.01); *A61B 5/6892* (2013.01); *A61N 1/3925* (2013.01); *A61N 1/3968* (2013.01); *A61B 2505/01* (2013.01); *A61B 2560/0443* (2013.01);

(Continued)

(58) Field of Classification Search

CPC ..................... A61M 2039/1077; A61B 5/6891
See application file for complete search history.

(56) References Cited

U.S. PATENT DOCUMENTS 7,957,798 B2 6/2011 Pearce et al.
8,738,128 B2 5/2014 Pearce et al.

(Continued)

*Primary Examiner* — Nathan R Price

(74) *Attorney, Agent, or Firm* — McDonnell Boehnen Hulbert & Berghoff LLP

(57) ABSTRACT

An example system for monitoring and delivering therapy to a patient includes a monitor module with patient monitoring capability, and a manifold that is operable to provide an electrical connection between the monitor module and cables connecting to sensors for collecting physiologic monitoring data of a patient, and to provide a gas connection between the monitor module and tubing for delivering treatment to or collecting additional physiologic monitoring data from the patient. The manifold includes a connector for mechanically connecting the manifold to the monitor module, and the connector also for mechanically disconnecting the manifold from the monitor module while maintaining the cables and the tubing coupled to the patient. In some examples, the system can also include a cot including a second set of monitoring electronics with patient monitoring capability, the cot including a port for coupling with the connector of the manifold.

20 Claims, 5 Drawing Sheets

Related U.S. Application Data

(60) Provisional application No. 62/954,051, filed on Dec. 27, 2019.

(51) Int. Cl.

| | |
|---|---|
| ***A61B 5/1455*** | (2006.01) |
| ***A61B 5/30*** | (2021.01) |
| ***A61B 5/308*** | (2021.01) |
| ***A61B 5/339*** | (2021.01) |
| ***A61N 1/39*** | (2006.01) |
| *A61M 16/04* | (2006.01) |

(52) U.S. Cl.

CPC ... *A61B 2562/222* (2013.01); *A61B 2562/227* (2013.01); *A61M 16/0463* (2013.01)

(56) References Cited

U.S. PATENT DOCUMENTS

| | | | |
|---|---|---|---|
| 8,880,168 | B2 | 11/2014 | Pearce et al. |
| 9,084,545 | B2 | 7/2015 | Sullivan et al. |
| 9,289,621 | B2 | 3/2016 | Aoyama et al. |
| 9,314,159 | B2 | 4/2016 | Lyon et al. |
| 9,339,661 | B2 | 5/2016 | Nova |
| 9,364,682 | B2 | 6/2016 | Peterson et al. |
| 9,439,572 | B2 | 9/2016 | Pearce et al. |
| 9,457,197 | B2 | 10/2016 | Aoyama et al. |
| 9,707,408 | B2 | 7/2017 | Peterson et al. |
| 9,713,728 | B2 | 7/2017 | Smith |
| 9,717,435 | B2 | 8/2017 | Walker et al. |
| 9,844,658 | B2 | 12/2017 | Jensen et al. |
| 9,872,998 | B2 | 1/2018 | Aoyama et al. |
| 9,907,971 | B2 | 3/2018 | Nova |
| 9,916,436 | B2 | 3/2018 | Bielstein |
| 9,994,315 | B2 | 6/2018 | Walker et al. |
| 10,068,667 | B2 | 9/2018 | Peterson et al. |
| 10,099,063 | B2 | 10/2018 | Peterson et al. |
| 10,105,546 | B2 | 10/2018 | Curtin et al. |
| 10,108,782 | B2 | 10/2018 | Curtin et al. |
| 10,118,048 | B2 | 11/2018 | Aoyama et al. |
| 10,124,181 | B2 | 11/2018 | Aoyama et al. |
| 10,124,184 | B2 | 11/2018 | Pearce et al. |
| 10,136,815 | B2 | 11/2018 | Lyon et al. |
| 10,159,846 | B2 | 12/2018 | Aoyama et al. |
| 12,329,717 | B2 * | 6/2025 | Benz .................... A61H 9/0092 |
| 2008/0281168 | A1 | 11/2008 | Gibson et al. |
| 2010/0114218 | A1 | 5/2010 | Heath |
| 2011/0030141 | A1 | 2/2011 | Soderberg et al. |
| 2012/0197665 | A1 | 8/2012 | Lewis et al. |
| 2014/0142647 | A1 | 5/2014 | McMahon et al. |
| 2014/0188516 | A1 | 7/2014 | Kamen et al. |
| 2014/0200464 | A1 | 7/2014 | Webster et al. |
| 2014/0272860 | A1 | 9/2014 | Peterson et al. |
| 2014/0278463 | A1 | 9/2014 | Merry et al. |
| 2015/0067021 | A1 * | 3/2015 | Protas .................... G16H 40/63 709/202 |
| 2015/0080655 | A1 | 3/2015 | Peterson et al. |
| 2015/0351643 | A1 | 12/2015 | Edwards et al. |
| 2016/0203304 | A1 | 7/2016 | Bielstein |
| 2016/0296167 | A1 | 10/2016 | Kantor et al. |
| 2016/0303389 | A1 | 10/2016 | Peterson et al. |
| 2016/0361556 | A1 | 12/2016 | Pearce et al. |
| 2017/0154160 | A1 | 6/2017 | Walker et al. |
| 2017/0215720 | A1 | 8/2017 | Walker et al. |
| 2017/0255755 | A1 | 9/2017 | Peterson et al. |
| 2017/0274215 | A1 | 9/2017 | Smith |
| 2018/0146874 | A1 | 5/2018 | Walker et al. |
| 2018/0199842 | A1 | 7/2018 | Walker et al. |
| 2020/0253474 | A1 | 8/2020 | Muhsin et al. |

* cited by examiner

METHODS AND SYSTEMS FOR MONITORING AND DELIVERING THERAPY TO A PATIENT INCLUDING A DETACHABLE MANIFOLD FOR A MONITOR MODULE

CROSS-REFERENCE TO RELATED APPLICATION

The present application is a continuation of and claims priority to U.S. application Ser. No. 17/065,765, filed on Oct. 8, 2020, which claims priority to U.S. provisional application No. 62/954,051, filed on Dec. 27, 2019, the entire contents of each of which are herein incorporated by reference.

BACKGROUND

Transport of patients after emergent care with a monitor and/or defibrillator can be difficult. Typically, following emergent care in which a monitor and/or defibrillator has been used for therapy, and wires, cables, and/or tubes are connected between the patient in the field and the monitor, the patient will then be transported to a hospital for further treatment. To do so, an ambulance arrives and a cot is used to move the patient to the ambulance. The patient, the monitor, and the cables and tubes connected to the patient must be moved as a unit onto the cot so as not to disturb on-going therapy or monitoring.

Generally, emergency medical technicians (EMTs) (or other ambulance crew) will lift the patient onto the cot, while another person simultaneously lifts the monitor and cables and places the monitor on the cot between the legs of the patient and thereafter attempts to organize the cables efficiently. Moving the entire monitor, defibrillator, cables, etc. from the patient's side to the cot can be problematic because the equipment can be quite large and heavy. However, in this manner, the monitor and defibrillator equipment remain attached to the patient as the patient is transported to the ambulance. The monitor then is moved to a more convenient spot in the ambulance once the cot arrives in the ambulance, but moving the monitor inside the ambulance can again be difficult due to the interconnecting cables and tubes (which often require reattachment after moving the monitor), limited space, and emergency situation. It is preferable, however, that the monitor and defibrillator remain connected to the patient to accompany the patient all the way to the hospital. Moreover, the monitor is moved again to move the cot and patient out of the ambulance and into a hospital treatment room, which under emergency situations, can create difficulties.

SUMMARY

Within examples described herein, systems and methods are described that include a monitor module with a detachable manifold operable to provide connections to cables and tubing coupled to a patient.

Within additional examples described herein, systems and methods are described for monitoring and delivering therapy to a patient.

Within additional examples described herein, systems and methods are described for a cot including monitoring electronics with patient monitoring capability.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Figure 1:
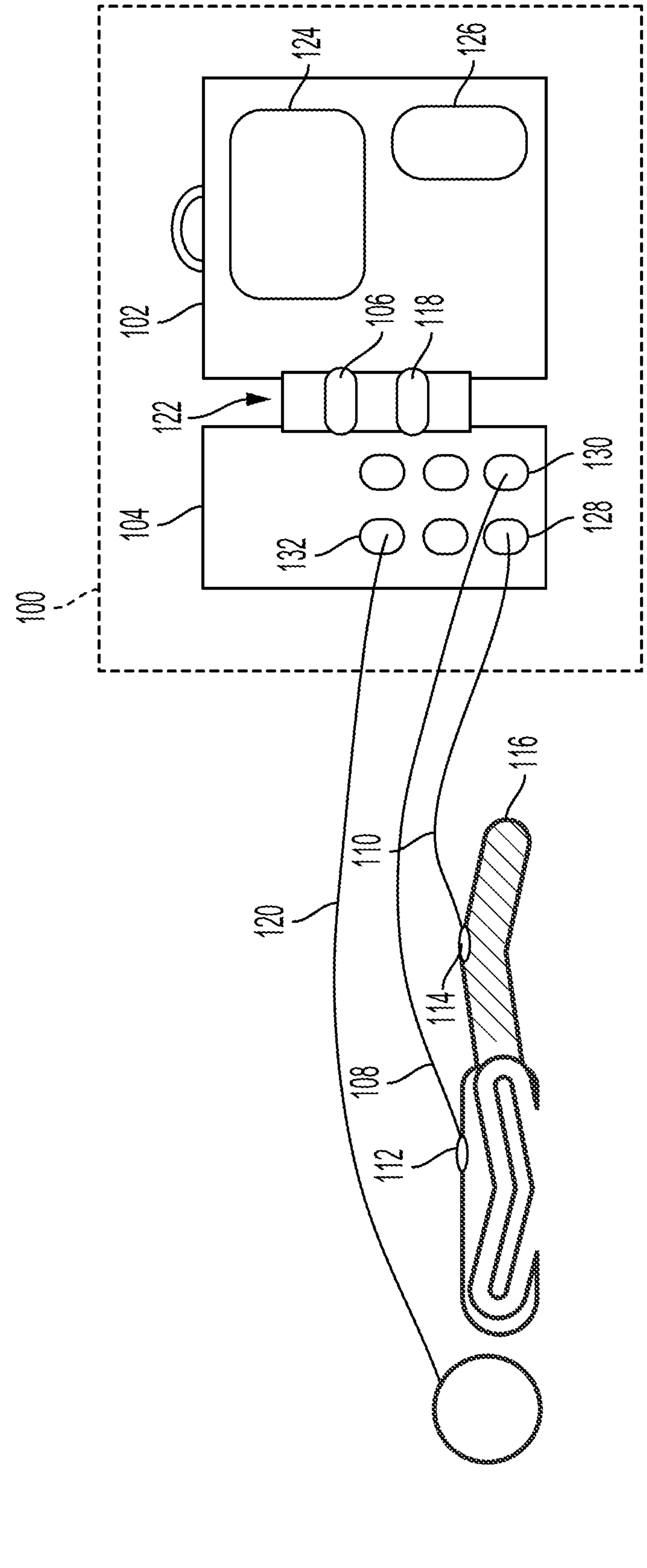
FIG. 1 illustrates an example system for monitoring and delivering therapy to a patient, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Example methods and systems describe solutions to cable and tube management issues when transporting a patient from the field to a cot and/or to an ambulance. An example system includes a detachable module that is operable to provide a connection between a monitor/defibrillator and cables/tubes used in the field, so that after connecting the cables/tubes to the patient in the field and using the monitor/defibrillator for therapy, the module detaches from the monitor while leaving the cables/tubes in place, and then connects to an outlet on a cot. The cot will be instrumented with battery/power to supply power to sensors/pumps, cables, or tubes connected to the patient. The cot can include other instrumentation as well so as to mimic or duplicate capabilities of the monitor component. For example, modules such as non-invasive blood pressure (NIBP) modules, $CO_2$ modules, $SPO_2$ modules, temperature modules, etc. can be included on the cot and coupled to a controller on the cot in communication with the outlet. In this manner, the detachable module unplugs from the external monitor/defibrillator and then is plugged into the outlet on the cot so that therapy and monitoring can continue without disruption and without a need to carry the heavy external monitor/defibrillator on or near the cot with the patient.

The external monitor can additionally include wireless communication capabilities, and can be in wireless communication with the controller on the cot as well to operate as an external display.

A second set of monitoring electronics can be implemented into the cot along with a power supply and Bluetooth or other wireless communication system. The detachable module or manifold enables easy transfer of the patient from the field to a cot. Once the manifold is connected to the cot, the cot can transmit information via a wireless link to the monitor for display and real-time and post-event data communication.

Implementing the detachable manifold enables all wires/tubes to remain connected to the patient and less disruption of therapy or monitoring during transfer of the patient. In addition, when arriving at the ambulance, there is no need to move the monitor again for secure placement since the monitor has been disconnected in the field.

In other examples, the detachable module enables connection to any outlet for continuing therapy and monitoring, such as an outlet in the ambulance or an outlet in the hospital, for example. The detachable module thus includes a manifold with a connector to enable communication and/or delivering of therapy through the wires and tubing.

Referring now to the figures, FIG. 1 illustrates an example system 100 for monitoring and delivering therapy to a patient, according to an example implementation. The system 100 includes a monitor module 102 with patient monitoring capability, and a manifold 104 that is operable to provide an electrical connection 106 between the monitor module 102 and cables 108 and 110 connecting to sensors 112 and 114 for collecting physiologic monitoring data of a patient 116, and to provide a gas connection 118 between the monitor module 102 and tubing 120 for delivering treatment to or collecting additional physiologic monitoring data from the patient 116. The manifold 104 includes a connector 122 for mechanically connecting the manifold 104 to the monitor module 102. The connector 122 is also adapted for mechanically disconnecting the manifold 104 from the monitor module 102 while maintaining the cables 108 and 110, and the tubing 120 coupled to the patient 116.

The monitor module 102 is shown to include a display 124 and (optionally) a user interface 126 (e.g., touchscreen, input buttons, etc.). The monitor module 102 may take many forms and may include other components. In one example, the monitor module 102 is a therapy module. An example therapy module includes a defibrillator or an automated external defibrillator (AED).

As devices become more integrated, the monitor module 102 may be capable of providing numerous functionalities. For example, in the healthcare related field, the monitor module 102 may have capabilities of providing a wide range of functionalities. Some examples of these functionalities include healthcare related functionalities such as, but not limited to, measuring/monitoring a patient's oxygen saturation level ($SpO_2$) via a pulse oximeter type device, a patient's heart activity (electrocardiogram (ECG)), a patient's brain activity such as, but not limited to electroencephalography (EEG), measuring/monitoring a patient's concentration or partial pressure of $CO_2$ such as, but not limited to, capnography capabilities (e.g., end-tidal carbon dioxide or ET $CO_2$), measuring/monitoring a patient's blood pressure such as, but not limited to, non-invasive blood pressure (NIBP) including continuous non-invasive arterial pressure (CNAP), invasive blood pressure, a patient's temperature, a patient's tissue oxygenation, and so forth.

However, more commonly, healthcare monitoring devices may include some of these example functionalities, while other healthcare monitoring devices may include some other or more sophisticated or specialized functionalities. In an example, the monitor module 102 may have the capability of providing limited functionality to defibrillation (e.g., automated external defibrillator or AED) In another example, the monitor module 102 may have the capability of providing basic life support (BLS) functionality. In yet another example, the monitor module 102 may include the capability to provide advanced life support (ALS) functionality. For the examples of BLS and ALS functionality, the monitor module 102 having the capability of providing BLS functionality may include defibrillator functionality and basic ECG functionality, while the monitor module 102 having the capability of providing ALS functionality may include, in addition to defibrillator functionality and basic ECG functionality, advanced airway management functionality, advanced cardiac monitors, advanced cardiac life support equipment, blood glucose testing equipment, capnography equipment, and any wide range of treatment options. Even more advanced functionalities can be included within the monitor module 102 such as, but not limited to, video related procedures (e.g., video laryngoscopy), intubation related procedures, ultrasound related procedures, telemedicine functionality (e.g., streaming video/audio with external imaging devices and built-in audio recording/playback devices), point of care lab analysis (e.g., blood and/or gas analysis), on-board electronic patient care recordation (e.g., electronic patient documentation), cardiopulmonary resuscitation feedback devices, ambient carbon monoxide monitoring, etc.

The manifold 104 is detachable from the monitor module 102, and the connector 122 may take the form of a plug connection that detaches all electronics and tubing with a single action. Thus, the manifold 104 enables disconnection of all the cables 108 and 110 and the tubing 120 from the monitor module 102 simultaneously. The connector 122 also provides mechanical attachment features to physically connect the manifold 104 to the monitor module 102.

The electrical connection 106 provides wiring necessary to enable transfer of data from the cables 108 and 110 to the manifold 104 and the monitor module 102. The cables 108 and 110 include one or more of electrocardiogram (ECG) cables, therapy pad cables, defibrillation cables, pacing cables, pulse oximetry cables, and temperature sensor cables, for example. The ECG monitoring cables can include a 12-lead ECG cable trunk and cable with 4-wire limb leads, a 12-lead ECG cable with 6-wire precordial attachment, a 3-wire ECG cable, a 5-wire ECG cable, and others for example.

The cables 108 and 110 connect to ports 128 and 130 on the manifold 104. The ports 128 and 130 may include plugs to connect the cables 108 and 110.

The sensors 112 and 114 output physiologic monitoring data measurements. Any number or type of sensors may be used depending on treatment or monitoring of the patient 116. In many instances, a variety of sensors is used to determine a variety of physiologic monitoring data. Physiologic monitoring data can include vital sign data (e.g., heart rate, respiration rate, blood pressure, and body temperature), as well as signals from other sensors described herein. In addition, physiologic monitoring data can also include treatment monitoring data, such as location at which an endotracheal tube has been placed or other sensor context information. The physiologic monitoring data can include timestamps associated with a time of collection and may be considered a measurement at a specific time. In some instances herein, physiologic monitoring data refers to one measurement and data associated with the one measurement, and in other instances, physiologic monitoring data refers to a collection of measurements as context indicates.

Example sensors include a temperature sensor to provide information indicative of a temperature, a light sensor to provide information indicative of ambient light, a camera to provide images indicative of placement of a tube for intubation in the patient 116, a carbon dioxide detector to provide an indication of carbon dioxide expelled by the patient 116, a microphone to provide an indication of sounds in the tube, a gas detector to provide an indication of presence of gases in the tube, a pressure sensor to provide an indication of airflow pressure in a tube for intubation in the patient 116, an air flow sensor to provide an indication of airflow in the tube, a pulse oximetry sensor to provide a measure of blood oxygenation in the patient 116, an oxygen sensor to provide an indication of oxygen inhaled and exhaled by the patient 116, an effective metabolic sensor (resulting from a combination of outputs from multiple sensors, such as an airway pressure sensor, airflow sensor, and capnography sensor, for example) to provide an indication of a metabolic rate of the patient 116, a blood pressure sensor to provide an indication of a blood pressure of the patient 116, a depth sensor to provide an indication of a depth of compression applied during cardiopulmonary resuscitation (CPR), an ultrasound sensor to provide an indication of vessel area and flow profile over time, external pressure sensors to provide tactile pressure applied to a chest of a patient during cardiopulmonary resuscitation (CPR), external ultrasound sensors to provide an indication of a location of a heart of the patient 116 and/or to assess whether the wall of the heart is moving, an electrocardiogram (ECG) sensor to provide one or more cardiac electrical signals, a lactate sensor to provide an indication of an analysis of blood of the patient 116, and a temperature sensor to provide an indication of patient temperature. Other types of sensors are possible as well to measure other physiologic monitoring data or vital signs of the patient 116.

Moreover, the sensors 112 and 114 can include communication interfaces to enable communication with the manifold 104 and the monitor module 102 over the cables 108 and 110 for a wired communication link.

The gas connection 118 provides a pathway necessary to enable airflow communication from the tubing 120 to the manifold 104 and the monitor module 102. The tubing 120 connects to a port 132 on the manifold 104. The port 132 may include a plug to connect the tubing 120. The tubing 120 includes one or more of a non-invasive blood pressure (NIBP) hose, an NIBP cuff, and intubation tubing for $CO_2$ measurements (or $CO_2$ measurements can also be sampled from other areas in which expired gases pass through, such as a nasal cannula), for example.

Figure 2:
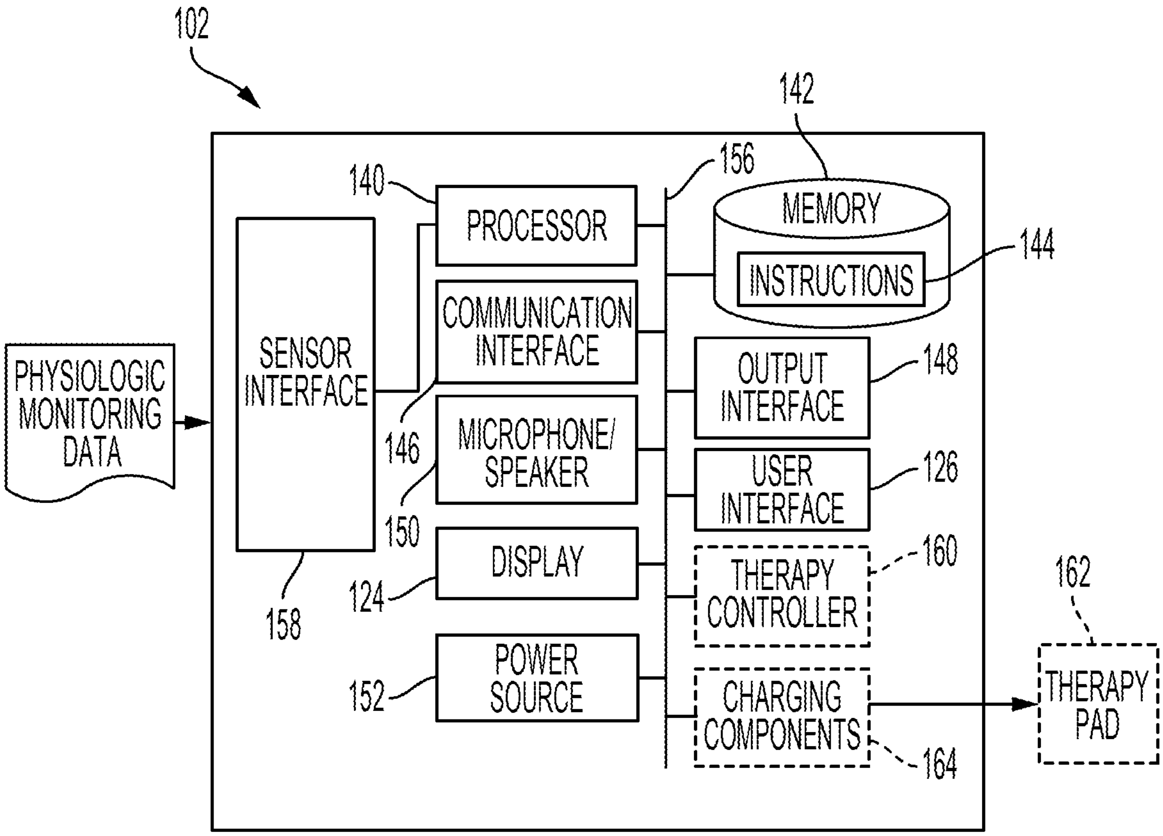
FIG. 2 illustrates a block diagram of an example of the monitor module, according to an example implementation.

FIG. 2 illustrates a block diagram of an example of the monitor module 102, according to an example implementation. In FIG. 2, the monitor module 102 includes a processor 140, and memory 142 storing instructions 144, that when executed by the processor 140, causes the processor 140 to perform functions of the monitor module 102.

To perform the functions, the monitor module 102 includes a communication interface 146, an output interface 148, the display 124, the user interface 126, a microphone/speaker 150, a power source 152, and each component of the monitor module 102 is connected to a communication bus 156. The monitor module 102 also includes a sensor interface 158.

The communication interface 146 may be one or more wireless interfaces and/or one or more wireline interfaces that allow for both short-range communication and long-range communication to one or more networks or to one or more remote devices. Such wireless interfaces may provide for communication under one or more wireless communication protocols, Bluetooth, Wi-Fi (e.g., an INSTITUTE OF ELECTRICAL AND ELECTRONIC ENGINEERS (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 146 may be configured to receive input data from the sensors 112 and 114 and may also be configured to send output data to other devices. The communication interface 146 thus may include hardware to enable communication between the monitor module 102 and other devices (not shown). The hardware may include transmitters, receivers, and antennas, for example. The communication interface 146 may also be capable of operating as a wireless access point as well.

The memory 142 may include one or more computer-readable storage media that can be read or accessed by the processor 140. The computer-readable storage media can include volatile and/or non-volatile storage components, such as optical, magnetic, organic or other memory or disc storage, which can be integrated in whole or in part with the processor 140. The memory 142 may be non-transitory data storage that is considered non-transitory computer readable media. In some examples, the non-transitory data storage can be implemented using a single physical device (e.g., one optical, magnetic, organic or other memory or disc storage unit), while in other examples, the non-transitory data storage can be implemented using two or more physical devices. The non-transitory data storage thus is a computer readable medium, and instructions 144 are stored thereon. The instructions 144 include computer executable code.

The processor 140 may be general-purpose processors or special purpose processors (e.g., digital signal processors, application specific integrated circuits, etc.). The processor 140 may receive inputs from the communication interface 146 as well as from other sensors and process the inputs to generate outputs that are stored in the non-transitory data storage. The processor 140 can be configured to execute the instructions 144 (e.g., computer-readable program instructions) that are stored in the non-transitory data storage and are executable to provide the functionality of the monitor or therapy module described herein.

The output interface 148 outputs information for reporting or storage, and thus, the output interface 148 may be similar to the communication interface 146 and can be a wireless interface (e.g., transmitter) or a wired interface as well.

The display 124 includes a (optionally) touchscreen or other type of display. The microphone/speaker 150 (optional) include capabilities to receive audio/voice instructions, and to output audio including audible prompts.

The power source 152 may include battery power, or a wired power means such as an AC or DC power connection to a power supply (e.g., such as a power supply in an ambulance).

The user interface 126 provides indicator LEDs for readiness status and power, to support failure analysis, operations, service, as well as software debugging. The user interface 126 may include Ethernet and USB ports as well.

The sensor interface 158 enables the connection of the manifold 104 to the monitor module 102. Thus, the sensor interface 158 attaches to the connector 122 for physical and communication connections. In one example, the electrical connection 106 plugs into an electrical port of the sensor interface 158, the gas connection 118 plugs into a gas port of the sensor interface 158, and the connector 122 physically attaches to a housing of the monitor module 102 to secure the manifold 104 to the monitor module 102. The connector 122 can include a snap fit and locking mechanism to mate with a snap fit and locking mechanism on the housing of the monitor module 102, for example.

The monitor module 102 can also include other components to operate as a therapy module, such as a therapy controller 160 that connects to therapy pads 162 and charging components 164. The therapy pads 162 are disposable and quickly connect/disconnect with a magnetic connection scheme, for example, to couple to the therapy controller 160. Electrical connection is made to carry the high currents required for defibrillation. The ability to read identification over a serial bus is designed into the connection. Thus, in this example, the monitor module 102 includes a therapy module with a defibrillator capability as a combined device that comprises a defibrillator operable to deliver therapy to the patient including one or more of defibrillation, pacing, and synchronized cardioversion according to therapy commands received from the processor 140 of the monitor module 102.

The therapy controller 160 may include a field programmable gate array (FPGA) state machine that receives high level commands from the processor 140. Such commands include charge to a certain energy level, shock, and discharge as well as setting a current level for pacing mode. The therapy controller 160 controls charging and discharging of an energy storage capacitor, detailed operation of the H-bridge (or any other means of connecting the capacitor to the patient), as well as the pacing circuitry that controls the current level within the charging components 164. A second FPGA state machine in the therapy controller 160 may be used to control analog-to-digital conversion of ECG and impedance waveforms so as to not burden the processor 140 with tight timing requirements. A circular buffer in the therapy controller 160 temporarily holds the data and alerts the processor 140 when another packet of predetermined size is available for transfer and processing.

Figure 3:
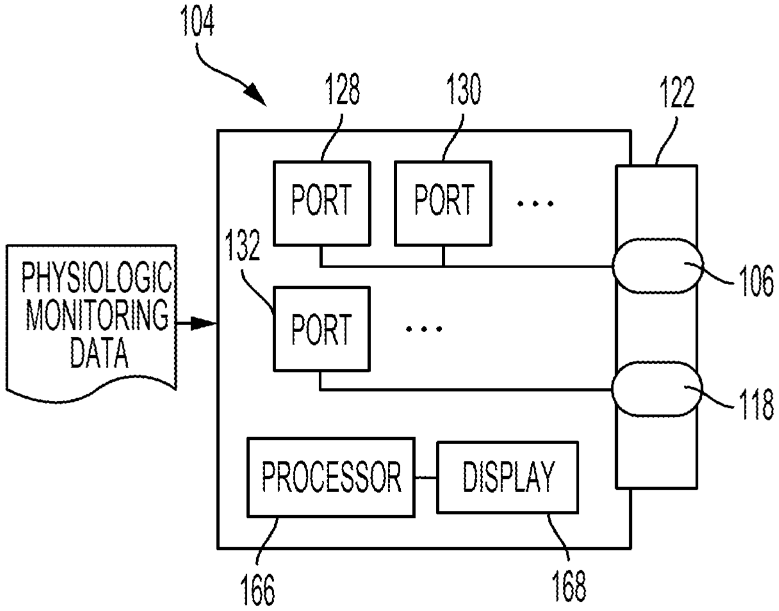
FIG. 3 illustrates a block diagram of an example of the manifold, according to an example implementation.

FIG. 3 illustrates a block diagram of an example of the manifold 104, according to an example implementation. The manifold 104 includes the ports 128 and 130 for connecting to the cables 108 and 110 and to provide a data communication pathway to the electrical connection 106. The ports 128 and 130 may thus include electrical plugs (female) for receiving corresponding electrical plugs (male) from the cables 108 and 110. Although only two electrical ports are shown, more or fewer may be included in the manifold 104.

The manifold 104 also includes the port 132 for connecting to the tubing 120 to provide a pathway for the gas connection 118. The port 132 may include a mechanical connector to receive a corresponding mechanical connector from the tubing 120. Although only one gas port is shown, more may be included in the manifold 104.

The manifold 104 may optionally also include a processor 166 connected to a display 168. The processor 166 can also has in input connected to each of the ports 128, 130, and 132, for example, to determine which (if any) of the ports have a cable to tube plugged in and to cause the display 168 to provide corresponding information. The display 168 may include an LCD screen or simply LEDs that are caused to light when a cable or tube is plugged or inserted into a corresponding port, for example.

The manifold 104 also includes the connector 122. The connector 122 may take many forms, and includes the electrical connection 106, the gas connection 118, and also a physical component for physically attaching to the monitor module 102.

The connector 122 may include a data connection, electrical power connection, hydraulic connection, and pneumatic connection, for example. The connector 122 can be a "zero insertion force" type of connector with a single twisting lock mechanism (and possible no larger than 5×1 inches), for example.

The manifold 104 may include a mating connector (attaching to the connector 122) and routing electronics and hoses to route signals and hoses to correct modules, for example.

The manifold 104 is lightweight and easily detachable from the monitor module 102. The manifold 104 may not include any power supply, but after connecting to the monitor module 102 or another outlet, the manifold 104 can (optionally) receive power from the device to which it connects.

Figure 4:
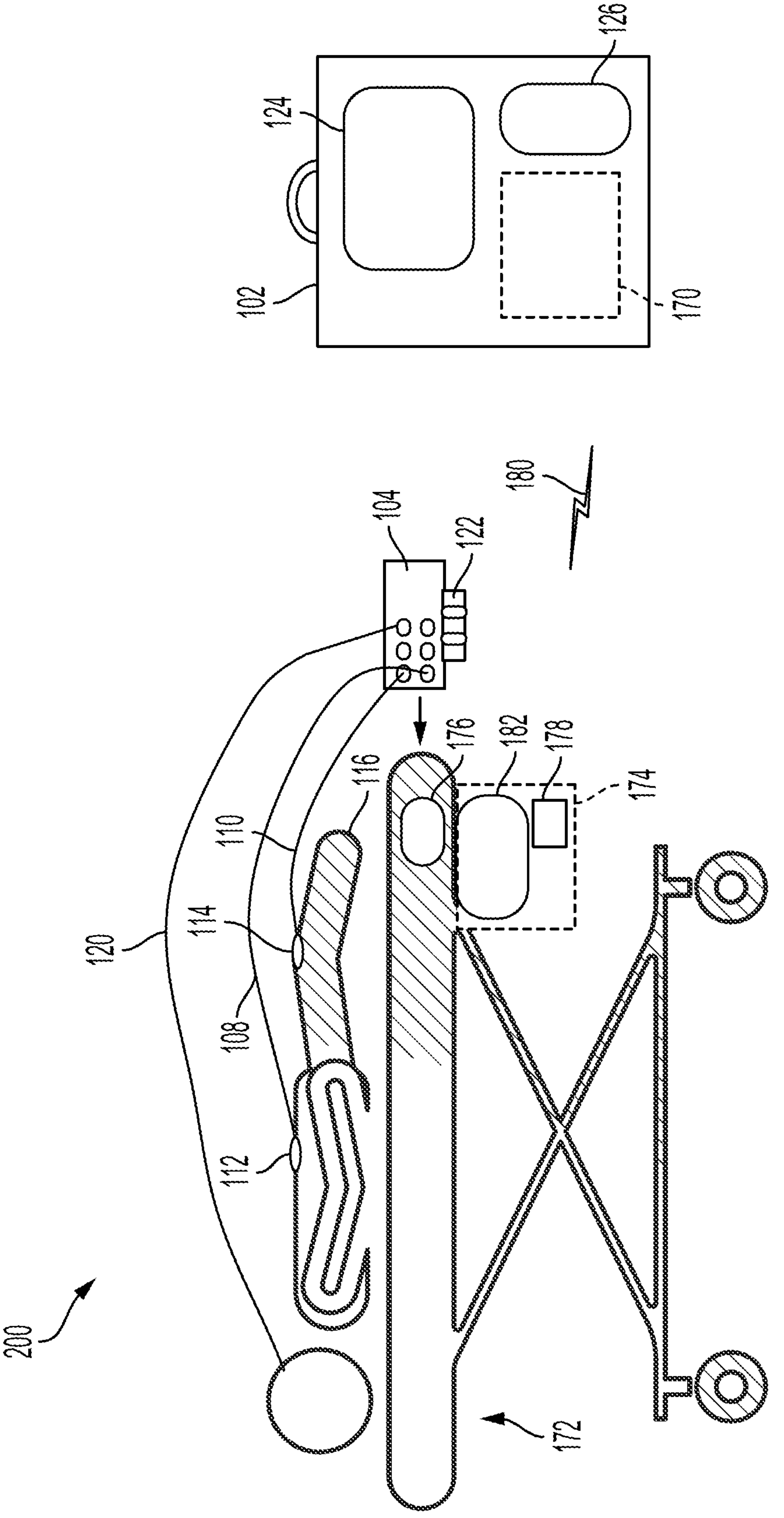
FIG. 4 illustrates a block diagram of another example of a system for monitoring and delivering therapy to the patient, according to an example implementation.

FIG. 4 illustrates a block diagram of another example of a system 200 for monitoring and delivering therapy to the patient 116, according to an example implementation. The system 200 includes the monitor module 102 including a first set of monitoring electronics 170 with patient monitoring capability, the manifold 104 that is operable to provide the electrical connection 106 between the monitor module 102 and cables 108 and 110 connecting to sensors 112 and 114 for collecting physiologic monitoring data of the patient 116. The manifold 104 includes the connector 122 for mechanically connecting the manifold 104 to the monitor module 102, and the connector 122 also for mechanically disconnecting the manifold 104 from the monitor module 102 while maintaining the cables 108 and 110 coupled to the patient 116. As described above, the manifold 104 is also operable to provide the gas connection 118 between the monitor module 102 and the tubing 120 for delivering treatment to or collecting additional physiologic monitoring data from the patient 116. In some examples, the manifold 104 is subdivided into components, with specific components providing separate connections to the monitor module 102 as well.

The system 200 also includes a cot 172 including a second set of monitoring electronics 174 with patient monitoring capability, and the cot 172 further includes a port 176 for coupling with the connector 122 of the manifold 104. The second set of monitoring electronics 174 on the cot 172 enable patient monitoring capability using inputs received via the manifold 104.

The cot 172 as shown is generally for moving the patient 116 more easily, and can include a bed portion connected to a structure with wheels, for example.

By utilizing the system 200, some problems with cable management are solved. For example, cables and tubing can remain in place connected or attached to the patient 116, and then when moving the patient 116 from the ground to the cot 172, the manifold 104 can be detached or disconnected from the monitor module 102 and then connected to the port 176 on the cot 172 seamlessly without any need to disconnect any other cables or tubing.

The monitor module 102 has the first set of monitoring electronics 170, which may include or refer to any and all components of the monitor module 102 shown and described with respect to FIG. 2. Such components include the display 124, the user interface 126, processor 140, the communication interface 146, the output interface 148, the therapy controller 160, and so forth. The cot 172 includes the second set of monitoring electronics 174, which can be a duplicate of the first set of monitoring electronics 170 as included in the monitor module 102 to replicate those components. In this manner, when the manifold 104 is disconnected from the monitor module 102 and plugged into the cot 172, there is no disruption in monitoring or treatment applied to the patient 116.

The cot 172 can further include a wireless communication interface 178 enabling transmission, via a wireless communication link 180, of the physiologic monitoring data to the monitor module 102. The wireless communication interface 178 is shown as included within the second set of monitoring electronics 174 on the cot 172, however, the wireless communication interface 178 may be included within a separate component as well.

The monitor module 102 also includes a wireless communication interface, such as provided by the communication interface 146 or output interface 148, to enable communication with the wireless communication interface 178 of the cot 172 over the wireless communication link 180.

The cot 172 also includes further includes a power supply 182 for providing power to the manifold 104 (e.g., for the second set of monitoring electronics 174), and optionally to the sensors 112 and 114 through the cables 108 and 110, for example. The power supply 182 is shown as included within the second set of monitoring electronics 174 on the cot 172, however, the power supply 182 may be included within a separate component or separately mounted on the cot 172 as well.

The cot 172 therefore includes all components needed to continue monitoring and treatment of the patient 116. For example, the cables 108 and 110 may include one or more of pulse oximetry cables and temperature sensor cables, and the tubing 120 can include a non-invasive blood pressure (NIBP) hose, and the cot 172 may thus include a non-invasive blood pressure (NIBP) module for receiving inputs via the manifold 104 from the non-invasive blood pressure (NIBP) hose, a pulse oximetry module for receiving inputs via the manifold 104 from the pulse oximetry cables, and a temperature module for receiving inputs via the 104 manifold from the temperature sensor cables. In another example, the cables 108 and 110 include one or more of electrical cables for capnograph and electrical cables for invasive pressure, and the tubing 120 includes tubes for capnography, and the cot 172 may thus include a non-invasive blood pressure (NIBP) module for receiving inputs via the manifold 104 from the electrical cables for invasive pressure, and a pulse oximetry module for receiving inputs via the manifold 104 from the electrical cables for capnograph and the tubes for capnography. Each different module may be included within the second set of monitoring electronics 174.

Figure 5:
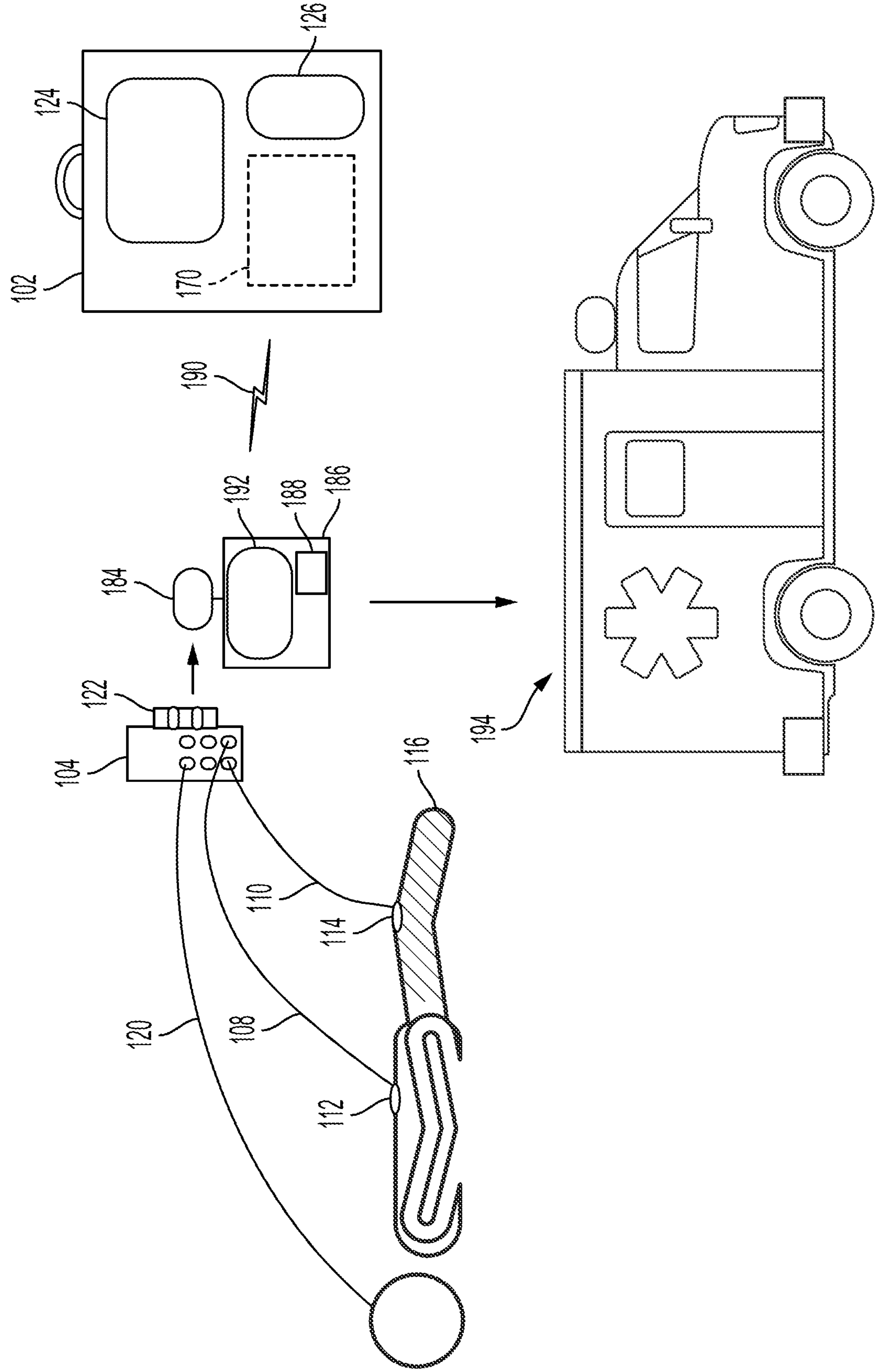
FIG. 5 illustrates a block diagram of another example of a system for monitoring and delivering therapy to the patient, according to an example implementation.

FIG. 5 illustrates a block diagram of another example of a system for monitoring and delivering therapy to the patient 116, according to an example implementation. In FIG. 5, an outlet 184 for coupling with the connector 122 of the manifold 104 following mechanical disconnection of the manifold 104 from the monitor module 102 is shown, and a controller 186 is coupled to the outlet 184 and include a wireless communication interface 188 enabling transmission, via a wireless communication link 190, of the physiologic monitoring data to the monitor module 102. As mentioned above, the monitor module 102 can further include a second wireless communication interface enabling wireless communication with the controller 186.

The controller 186 may further include a display 192 to illustrate data being received, or sensors in operation and connected to the manifold 104, for example.

In FIG. 5, the outlet 184 is included in an ambulance 194. In this example, the patient 116 may be brought to the ambulance, via the cot 172, and then the manifold 104 is disconnected from the cot 172 or disconnected from the monitor module 102 and connected to the outlet 184 in the ambulance so that monitoring and treatment of the patient 116 is uninterrupted and all cabling and tubing can remain connected to the patient 116 during transfer of the patient 116.

The ambulance 194 may not include any internal displays, and the monitor module 102 further includes the display 124 which can operate as an external display for the outlet 184 by displaying information indicative of the physiologic monitoring data received via the wireless communication link 190, for example, as well as control. The monitor module 102 can be secured inside the ambulance 194 at any position and then receive the data wirelessly for display.

In some examples, the manifold 104 can remain connected to the cot 172, and the patient 116 is positioned in the ambulance 194 on the cot 172. Due to the wireless link, the monitor 102 would continue to display physiological parameters received from the cot 172. The monitor 102 can be positioned in a convenient location inside the ambulance for viewing during transport, for example.

The outlet 184 may alternatively be included in other vehicles or other areas as well. For example, the outlet 184 may be included in an emergency room of a hospital or treatment room of a doctor's office. The patient 116 can then be transported to one of these rooms and monitoring and treatment can continue uninterrupted by plugging the manifold 104 into the outlet 184.

Figure 6:
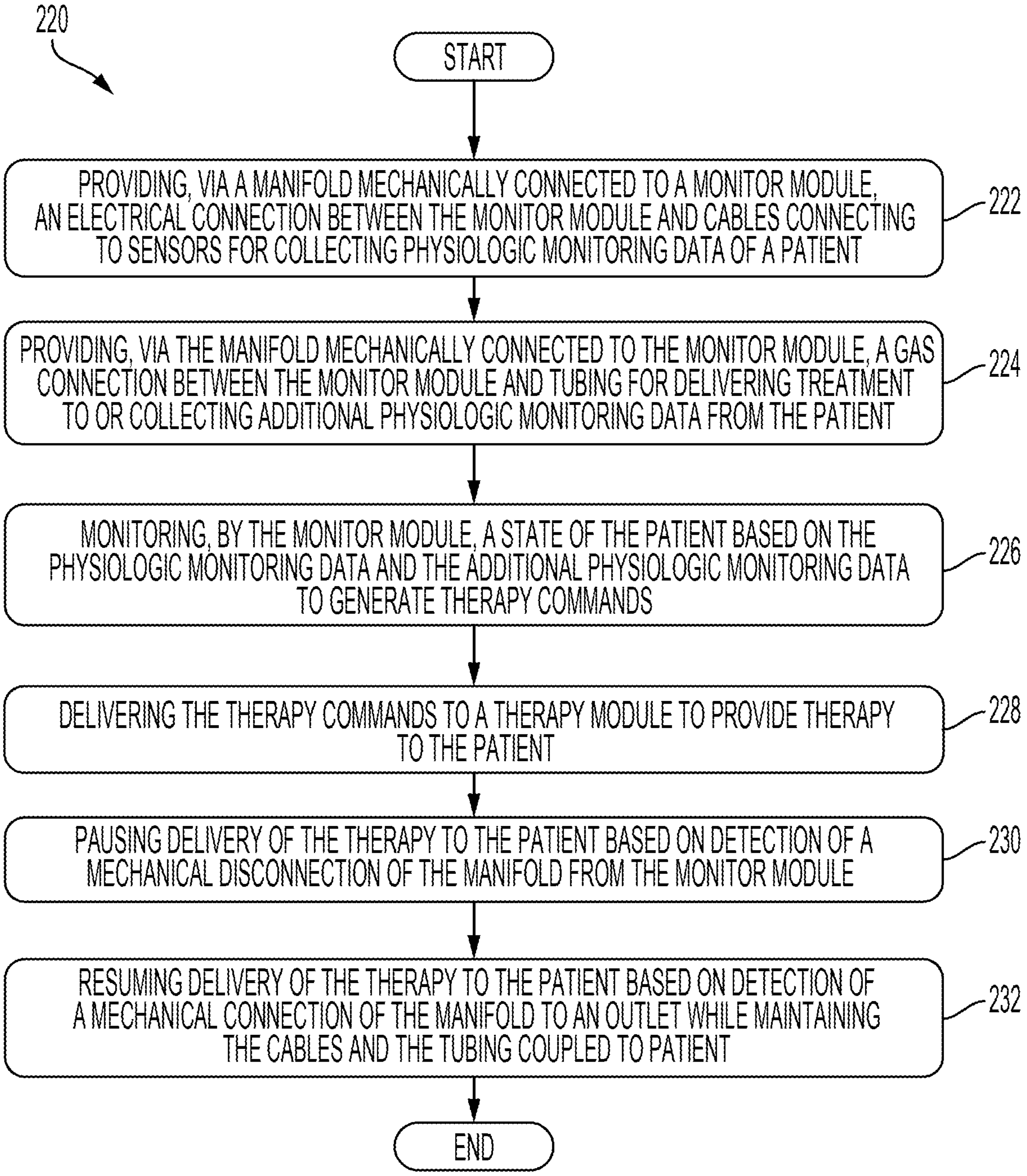
FIG. 6 shows a flowchart of another example of a method for monitoring and delivering therapy to the patient, according to an example implementation.

FIG. 6 shows a flowchart of another example of a method 220 for monitoring and delivering therapy to the patient 116, according to an example implementation. Method 220 shown in FIG. 6 presents an example of a method that could be used with the system 100 shown in FIG. 1 (or with the monitor module 102 shown in FIG. 1), and with the system 200 shown in FIG. 4, for example. Further, devices or systems may be used or configured to perform logical functions presented in FIG. 6. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 220 may include one or more operations, functions, or actions as illustrated by one or more of blocks 222-232. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example. The program code may also be downloaded from the monitor, which has connections to the Internet for updates, for example.

In addition, each block or portions of each block in FIG. 6, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 222, the method 220 includes providing, via a manifold mechanically connected to a monitor module, an electrical connection between the monitor module and cables connecting to sensors for collecting physiologic monitoring data of a patient.

At block 224, the method 220 includes providing, via the manifold mechanically connected to the monitor module, a gas connection between the monitor module and tubing for delivering treatment to or collecting additional physiologic monitoring data from the patient.

At block 226, the method 220 includes monitoring, by the monitor module, a state of the patient based on the physiologic monitoring data and the additional physiologic monitoring data to generate therapy commands. The monitor module as shown in FIG. 2 may include the instructions 144 executable by the processor 140 to receive the physiologic monitoring data and generate output signals indicating the state of the patient 116. The output signals may be specific to monitored vital signs, such as heart rate, blood pressure, etc., or detailed analysis of the data to provide a diagnosis of the patient 116, for example.

At block 228, the method 220 includes delivering the therapy commands to a therapy module to provide therapy to the patient. In an example where the monitor module 102 includes a therapy module with a defibrillator capability, example therapy commands can include commands to provide defibrillation, pacing, and synchronized cardioversion.

At block 230, the method 220 includes pausing delivery of the therapy to the patient based on detection of a mechanical disconnection of the manifold from the monitor module. The monitor module 102 or the manifold 104 may detect disconnection of the connector 122 via electrical disconnection, and responsively pause display of monitoring information and algorithms based on that information and/or delivery of the therapy or therapy commands and pause monitoring as well. The manifold 104 may be disconnected from the monitor module 102 when moving the patient 116 onto a cot 172, or into an ambulance 194, for example. During that time, the patient 116 remains connected to the cables and tubing.

Thus, the monitor module 102 is in communication with the therapy module and the monitor module 102 has a non-transitory computer-readable medium with a plurality of executable instructions stored therein and the processor adapted to execute the plurality of executable instructions to pause delivery of therapy to the patient 116 via the therapy module based on detection of a mechanical disconnection of the manifold 104 from the monitor module 102.

At block 232, the method 220 includes resuming delivery of the therapy to the patient based on detection of a mechanical connection of the manifold to an outlet while maintaining the cables and the tubing coupled to patient. The manifold 104 or the controller 186 may detect the connection of the manifold 104 to the outlet 184 via an electrical connection, and then cause the therapy and monitoring to resume. In additional examples, the method 220 thus also includes disconnecting the manifold from the monitor module while maintaining the cables and the tubing coupled to the patient, and connecting the manifold to the outlet.

In one example, the method 220 includes resuming delivery of the therapy to the patient 116 based on detection of the mechanical connection of the manifold 104 to the cot 172 including the second set of monitoring electronics 174, and the second set of monitoring electronics on the cot 172 enable patient monitoring capability using inputs received via the manifold 104.

To perform monitoring or delivery of therapy to the patient 116, in some examples, the method 220 includes receiving inputs at the cot 172 via the manifold 104 from a non-invasive blood pressure (NIBP) hose, receiving inputs at the cot 172 via the manifold 104 from pulse oximetry cables, and receiving inputs at the cot 172 via the manifold 104 from temperature sensor cables. Depending on the monitoring or therapy being provided, other cables may be included as well.

In further examples, the method 220 also includes wirelessly transmitting, via a wireless communication interface of a controller coupled to the outlet, the physiologic monitoring data to the monitor module, such as described with respect to FIG. 5.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A system for monitoring and delivering therapy to a patient, the system comprising:

a monitor module with patient monitoring capability and a therapy module with a defibrillator capability, wherein the monitor module and the therapy module are a combined device which comprises a defibrillator operable to deliver therapy to the patient including one or more of defibrillation, pacing, and synchronized cardioversion according to therapy commands received from the monitor module, wherein the monitor module is in communication with the therapy module; and a manifold that is operable to provide a gas connection between the monitor module and tubing, wherein the gas connection is for delivering treatment to or collecting gases from the patient via the tubing, wherein the manifold includes a connector for mechanically connecting the manifold to the monitor module, and the connector is also for mechanically disconnecting the manifold from the monitor module while maintaining the tubing coupled to the patient, wherein the monitor module has a non-transitory computer-readable medium with a plurality of executable instructions stored therein and a processor adapted to execute the plurality of executable instructions to:

pause delivery of therapy to the patient via the therapy module based on detection of a mechanical disconnection of the manifold from the monitor module; and resume delivery of the therapy to the patient based on detection of a mechanical connection of the manifold to an outlet while maintaining the tubing coupled to the patient.

2. The system of claim 1, wherein the tubing includes multiple tubes, and wherein the manifold enables disconnection of all the multiple tubes from the monitor module simultaneously.

3. The system of claim 1, wherein the gas connection provides a pathway to enable airflow communication from the tubing to the manifold and the monitor module.

4. The system of claim 1, wherein the tubing includes one or more of a non-invasive blood pressure (NIBP) hose, an NIBP cuff, and intubation tubing.

5. The system of claim 1, wherein the monitor module includes a first set of monitoring electronics, and the system further comprises:

a cot including a second set of monitoring electronics, the cot further including a port for coupling with the connector of the manifold, wherein the second set of monitoring electronics on the cot enable patient monitoring capability using inputs received via the manifold, wherein the cot is for moving the patient.

6. The system of claim 5, wherein the monitor module is configured to wirelessly receive data from the cot and operate as an external display for the cot by displaying the data independently processed by the second set of monitoring electronics.

7. The system of claim 1, further comprising:

a cot for moving the patient, wherein the cot includes:

a port for coupling with the connector of the manifold; and a wireless communication interface enabling transmission, via a wireless communication link, of data to another device.

8. The system of claim 7, wherein the cot further comprises a power supply for providing power to the manifold.

9. The system of claim 7, wherein the tubing includes tubes for capnography, and the cot further comprises:

a pulse oximetry module for receiving inputs via the manifold from the tubes for capnography.

10. The system of claim 1, further comprising:

the outlet for coupling with the connector of the manifold following mechanical disconnection of the manifold from the monitor module; and a controller coupled to the outlet and including a wireless communication interface enabling transmission, via a wireless communication link, of physiologic monitoring data to the monitor module.

11. The system of claim 10, wherein the monitor module further includes a second wireless communication interface enabling wireless communication with the controller.

12. The system of claim 11, wherein the monitor module further includes a display to operate as an external display for the outlet by displaying information indicative of the physiologic monitoring data received via the wireless communication link.

13. The system of claim 10, wherein the outlet is included in an ambulance.

14. The system of claim 1, wherein the manifold further includes a second processor and a display supported thereon, wherein the second processor configured to determine which of a plurality of sensors are coupled to the manifold and cause the display to provide information identifying the sensors.

15. The system of claim 1, wherein the manifold is configured to be devoid of an internal power supply and is configured to receive power from the monitor module upon the mechanical connection.

16. The system of claim 1, wherein the monitor module comprises a therapy controller in communication with the processor, and wherein the plurality of executable instructions are further executable to generate a safety interlock signal to pause a high-energy shock command loop of the therapy controller during mechanical disconnection of the manifold.

17. The system of claim 1, wherein the processor is further adapted to execute instructions to associate timestamps with physiologic monitoring data to synchronize data collection before, during, and after mechanical disconnection to maintain a continuous electronic patient care record.

18. The system of claim 1, wherein the connector of the manifold is configured to simultaneously engage both an electrical interface and a pneumatic interface with the monitor module.

19. A system for monitoring and delivering therapy to a patient, the system comprising:

a monitor module including a first set of monitoring electronics with patient monitoring capability and a battery for powering the monitor module;

a manifold that is operable to provide a gas connection between the monitor module and tubing, wherein the gas connection is for delivering treatment to or collecting gases from the patient via the tubing, wherein the manifold includes a connector for mechanically connecting the manifold to the monitor module, and the connector is also for mechanically disconnecting the manifold from the monitor module while maintaining the tubing coupled to the patient; and a cot including a second set of monitoring electronics with patient monitoring capability and a power supply for powering the second set of monitoring electronics, the cot further including a port for coupling with the connector of the manifold, wherein the second set of monitoring electronics on the cot enable patient monitoring capability using inputs received via the manifold to independently process physiologic monitoring data received through the manifold upon mechanical disconnection of the manifold from the monitor module and mechanically connecting the manifold to the port.

20. The system of claim 19, wherein the cot further comprises:

a wireless communication interface enabling transmission, via a wireless communication link, of data to the monitor module.

* * * * *